United States Patent
Collins et al.

(10) Patent No.: US 6,701,591 B2
(45) Date of Patent: Mar. 9, 2004

(54) DIAPHANOUS NONWOVEN FABRICS WITH IMPROVED ABRASIVE PERFORMANCE

(75) Inventors: David Collins, Apex, NC (US); Charles Keith Curtis, Benson, NC (US); Jerry Parker, Benson, NC (US)

(73) Assignee: Polymer Group, Inc., North Charleston, SC (US)

( * ) Notice: Subject to any disclaimer, the term of this patent is extended or adjusted under 35 U.S.C. 154(b) by 4 days.

(21) Appl. No.: 10/251,746

(22) Filed: Sep. 20, 2002

(65) Prior Publication Data

US 2003/0079324 A1 May 1, 2003

Related U.S. Application Data

(60) Provisional application No. 60/324,192, filed on Sep. 21, 2001.

(51) Int. Cl.[7] .................................. D04H 1/46
(52) U.S. Cl. ........................................................ 28/104
(58) Field of Search .......................... 28/104, 105, 106, 28/167, 163; 442/408, 384, 385, 387, 389, 390, 415, 416; 156/148

(56) References Cited

U.S. PATENT DOCUMENTS

| | | |
|---|---|---|
| 3,485,706 A | 12/1969 | Evans |
| 4,228,123 A | 10/1980 | Marshall |
| 4,555,430 A | 11/1985 | Mays |
| 4,612,226 A | 9/1986 | Kennette et al. |
| 4,693,922 A | 9/1987 | Buyofsky et al. |
| 4,735,842 A | 4/1988 | Buyofsky et al. |
| 5,009,652 A | 4/1991 | Morgan et al. |
| 5,071,648 A | 12/1991 | Rosenblatt |
| 5,098,764 A | 3/1992 | Bassett et al. |
| 5,144,729 A * | 9/1992 | Austin et al. ................ 28/105 |
| 5,238,644 A | 8/1993 | Boulanger et al. |
| 5,244,711 A | 9/1993 | Drelich et al. |
| 5,320,900 A * | 6/1994 | Oathout ........................ 28/104 |
| 5,433,987 A * | 7/1995 | Peterson et al. .............. 28/104 |
| 5,459,912 A * | 10/1995 | Oathout ........................ 28/105 |
| 5,648,141 A | 7/1997 | Butterworth et al. |
| 5,822,823 A | 10/1998 | Polzin et al. |
| 5,827,597 A | 10/1998 | James et al. |
| 6,007,653 A | 12/1999 | Pirinen et al. |
| 6,022,818 A * | 2/2000 | Welchel et al. ............. 442/384 |
| 6,117,515 A | 9/2000 | Brunson et al. |
| 6,199,533 B1 | 3/2001 | Morris et al. |
| 6,267,743 B1 | 7/2001 | Bodenschatz et al. |
| 6,290,663 B1 | 9/2001 | Darcey |
| 6,306,234 B1 * | 10/2001 | Barker et al. ................. 28/104 |
| 6,375,773 B1 * | 4/2002 | Andersen ..................... 156/148 |
| 6,381,817 B1 * | 5/2002 | Moody, III ................... 28/104 |
| 6,460,233 B2 * | 10/2002 | Noelle ........................... 28/104 |

* cited by examiner

Primary Examiner—A. Vanatta
(74) Attorney, Agent, or Firm—Wood, Phillips, Katz, Clark & Mortimer

(57) ABSTRACT

In the present invention, a hydroentangled and three-dimensionally patterned fibrous material is formed from a fibrous matrix to produce a nonwoven fabric of pronounced open area and enhanced physical properties, including abrasive, and particularly wet abrasive, performance. A three-dimensional pattern utilized on the forming surface results in the nonwoven fabric having a diaphanous gauze-like or cheesecloth-like presentation.

A method of making a nonwoven material embodying the principles of the present invention contemplates the use of staple length fibers to facilitate economical fabric formation. Formation of the fibrous nonwoven fabric on a three-dimensional, image transfer device by hydroentangling imparts desired physical properties to the fabric such as the controlled placement of the fiber population relative to the desired three-dimensional pattern of the imaging device. This nonwoven fabric may be natural or colored.

10 Claims, 2 Drawing Sheets

DIAPHANOUS NONWOVEN FABRICS WITH IMPROVED ABRASIVE PERFORMANCE

TECHNICAL FIELD

The present invention relates generally to a nonwoven fabric, and specifically, to a nonwoven fabric having imparted therein a diaphanous bundled fiber pattern, whereby the nonwoven fabric exhibits an improved abrasive surface and high absorbency for use in cleaning, scrubbing, and wound debridement

BACKGROUND OF THE INVENTION

Diaphanous materials routinely used in cleaning and medical applications include the use of "gauze" or "cheesecloth" like materials. These materials are typically manufactured by conventional textile fabric processes.

The production of conventional textile fabrics is known to be a complex, multi-step process. The production of fabrics from staple fibers begins with the carding process where the fibers are opened and aligned into a feedstock known as sliver. Several strands of sliver are then drawn multiple times on drawing frames to further align the fibers, blend, improve uniformity as well as reduce the diameter of the sliver. The drawn sliver is then fed into a roving frame to produce roving by further reducing its diameter as well as imparting a slight false twist. The roving is then fed into the spinning frame where it is spun into yarn. The yarns are next placed onto a winder where they are transferred into larger packages. The yarn is then ready to be used to create a fabric.

For a woven fabric, the yarns are designated for specific use as warp or fill yarns. The fill yarn packages (which run in the cross direction and are known as picks) are taken straight to the loom for weaving. The warp yarns (which run on in the machine direction and are known as ends) must be further processed. The packages of warp yarns are used to build a warp beam. Here the packages are placed onto a warper, which feeds multiple yarn ends onto the beam in a parallel array. The warp beam yarns are then run through a slasher where a water-soluble sizing is applied to the yarns to stiffen them and improve abrasion resistance during the remainder of the weaving or knitting process. The yarns are wound onto a loom beam as they exit the slasher, which is then mounted onto the back of the loom. Here the warp and fill yarns are interwoven or knitted in a complex process to produce yardages of cloth.

The complexities inherent to woven textile processes in gauze or cheesecloth manufacture have been recognized as a critical limitation to efficient manufacture. The production of nonwoven fabrics from staple fibers is known to be more efficient than traditional textile processes as the fabrics are produced directly from the carding process. Nonwoven fabrics are suitable for use in a wide variety of applications where the efficiency with which the fabrics can be manufactured provides a significant economic advantage for these fabrics versus traditional textiles. Hydroentangled fabrics have been developed with improved properties that are a result of the entanglement of the fibers or filaments in the fabric providing improved fabric integrity. U.S. Pat. No. 3,485,706, to Evans, hereby incorporated by reference, discloses processes for effecting hydroentanglement of nonwoven fabrics. More recently, hydroentanglement techniques have been developed which impart images or patterns to the entangled fabric by effecting hydroentanglement on three-dimensional image transfer devices. Such three-dimensional image transfer devices are disclosed in U.S. Pat. No. 5,098,764, hereby incorporated by reference, with the use of such image transfer devices being desirable for providing a fabric with enhanced physical properties.

Prior art attempts to manufacture suitable diaphanous nonwoven fabrics for cleaning and medical applications have met with limited success. U.S. Pat. No. 4,555,430 to Mays, describes the use of staple length fibers in two different staple length populations and a thermoplastic binding component. U.S. Pat. No. 4,612,226 to Kennette et al., describes a wiping cloth having high abrasion resistance through the use of adhesive binder chemistry. U.S. Pat. Nos. 4,693,922 and 4,735,842, to Buyofsky et al., describe lightweight materials having a preponderance of thermoplastic staple fibers. The aforementioned U.S. Pat. No. 5,098,764, is directed to a nonwoven fabric whereby specific fibrous geometries are necessary for fabric performance. U.S. Pat. No. 5,648,141, to Butterworth et al., incorporated herein by reference, describes a debridement sponge manufactured from apertured nonwoven fabric.

An unmet need exists for a diaphanous nonwoven fabric, suitable for cleaning and medical applications, whereby a combination of fiber selection and performance attributes is obtained without the necessary use of binder or binding component.

SUMMARY OF THE INVENTION

In the present invention, a hydroentangled and three-dimensionally patterned fibrous material is formed from a fibrous matrix to produce a nonwoven fabric of pronounced open area and enhanced physical properties, including abrasive, and particularly wet abrasive, performance. A three-dimensional pattern utilized on the forming surface results in the nonwoven fabric having a diaphanous gauze-like or cheesecloth-like presentation.

A method of making a nonwoven material embodying the principles of the present invention contemplates the use of staple length fibers to facilitate economical fabric formation. Formation of the fibrous nonwoven fabric on a three-dimensional, image transfer device by hydroentangling imparts desired physical properties to the fabric such as the controlled placement of the fiber population relative to the desired three-dimensional pattern of the imaging device. This nonwoven fabric may be natural or colored.

A method of making a nonwoven fabric in accordance with the present invention includes providing a precursor web comprising staple length fibers. Fibers can comprise thermoplastic, thermoset, or natural fiber compositions. Preferred thermoplastic fiber composition include; polyester, polyolefin, polyamide, and the blends thereof. Natural fibers of particular interest are cotton fibers, in either virgin or recycled form.

Suitable mechanism of forming such precursor webs includes: carded fibrous batt, cross lapped fibrous batts, air-randomized fibrous batts, consolidated non-woven fabric, and combinations thereof. A preferable method of forming a suitable precursor web is through the pre-entanglement of staple fibers on a foraminous forming surface through the use of high-pressure water jets.

The present method further entails the provision of a three-dimensional, image transfer device having an array of three-dimensional surface elements thereon. The precursor web is positioned on the image transfer device, and hydroentangled to form the diaphanous nonwoven fabric.

The performance of the nonwoven fabric can be altered by varying the blend ratio of the thermoplastic fiber to the natural fiber used in the manufacture of the fabric. Sufficient absorbency, while maintaining durable wet abrasive performance, can be obtained by using no less than about 50% by weight natural fiber, the remainder of the weight-comprising polymer staple fibers. The nonwoven fabric can also comprise multiple layers of either blended fibrous components, or, preferably, the layering of one or more fibrous layers, which can be of either homogenous or heterogeneous composition.

The present invention further contemplates the addition of a physical performance modifying chemistries into or upon either one or more of the fibrous components or to the resulting nonwoven fabric.

DETAILED DESCRIPTION

Figure 1:
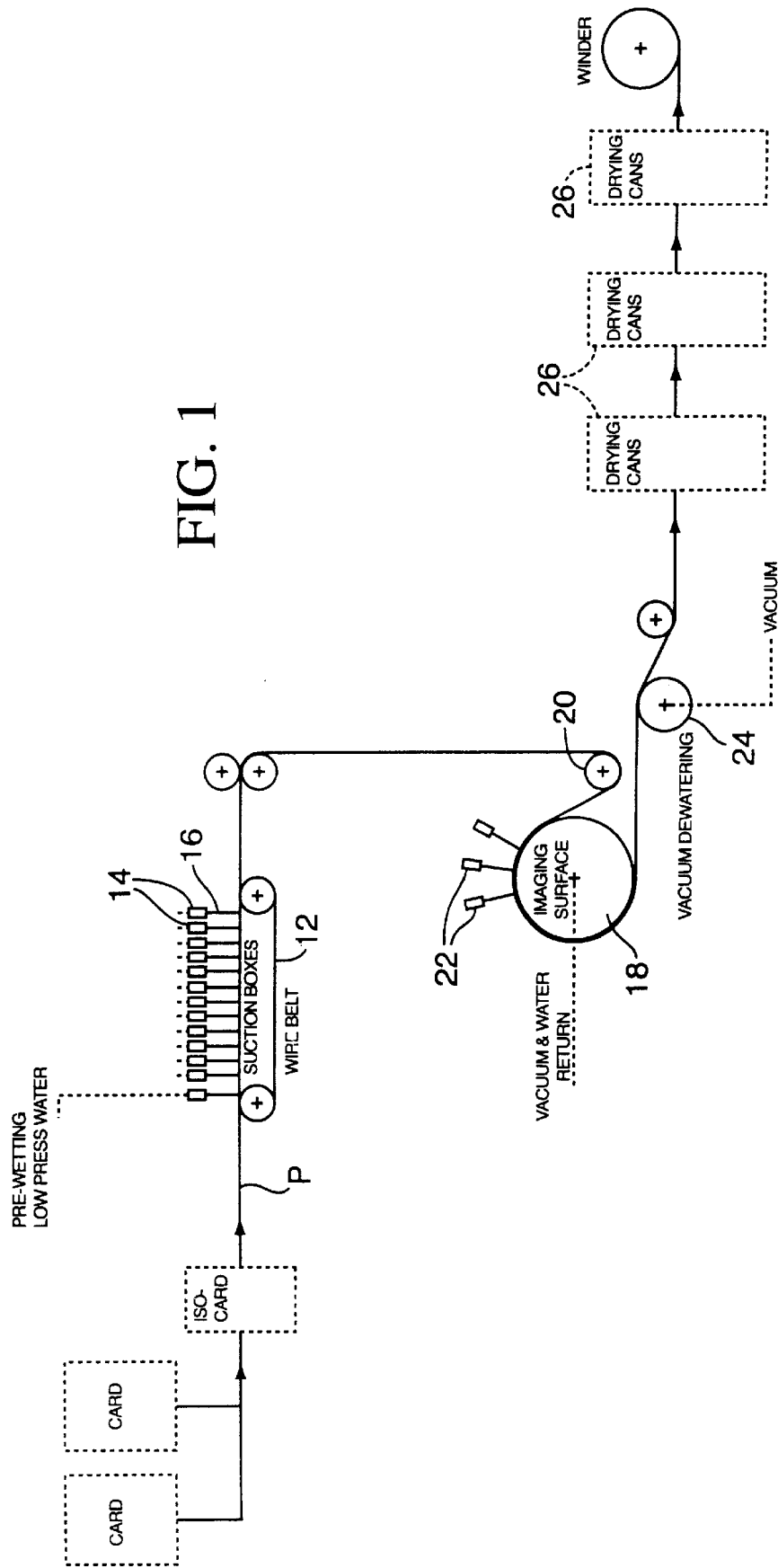
FIG. 1 is a diagrammatic view of an apparatus for manufacturing a nonwoven facing fabric embodying the principles of the present invention, and includes a schematic of the process steps for the manufacture of the colored composite.

While the present invention is susceptible of embodiment in various forms, there is shown in the drawings, and will hereinafter be described, a presently preferred embodiment of the invention, with the understanding that the present disclosure is to be considered as an exemplification of the invention, and is not intended to limit the invention to the specific embodiment illustrated.

The present invention is directed to a method of forming nonwoven fabrics, such nonwoven fabrics being produced by hydroentanglement, wherein imaging and patterning of the fabrics is enhanced by hydroentanglement on a three-dimensional image transfer device. Such imaged hydroentangled fabrics comprise a combination of natural and synthetic staple fibers, which in combination with the diaphanous pattern, results in a material exhibiting combined absorbency and wet-abrasive qualities as to render it suitable for application in cleaning and medical applications.

The performance of the nonwoven fabric can be altered by varying the blend ratio of the thermoplastic fiber to the natural fiber used in the manufacture of the fabric. Sufficient absorbency, while maintaining durable wet abrasive performance, can be obtained by using no less than about 50% by weight natural fiber, the remainder of the weight-comprising polymer staple fibers. The nonwoven fabric can also comprise multiple layers of either blended fibrous components, or, preferably, the layering of one or more fibrous layers, which can be of either homogenous or heterogeneous composition.

With particular reference to FIG. 1, therein is illustrated an apparatus for practicing the method of the present invention for forming a nonwoven fabric. The fabric is formed from a fibrous matrix, which comprises fibers selected to promote economical manufacture. The fibrous matrix can be carded and optionally air-randomized to form a precursor web, designated P.

FIG. 1 illustrates a hydroentangling apparatus for forming nonwoven fabrics in accordance with the present invention. The apparatus includes a foraminous-forming surface in the form of a flat bed entangler 12 upon which the precursor web P is positioned for pre-entangling. Precursor web P is then sequentially passed under entangling manifolds 14, whereby the precursor web is subjected to high-pressure water jets 16. This process is well known to those skilled in the art and is generally taught by U.S. Pat. No. 3,485,706, to Evans, hereby incorporated by reference.

The entangling apparatus of FIG. 1 further includes an imaging and patterning drum 18 comprising a three-dimensional image transfer device for effecting imaging and patterning of the now-entangled precursor web. After pre-entangling, the precursor web is trained over a guide roller 20 and directed to the image transfer device 18, where a three-dimensional image is imparted into the fabric on the foraminous-forming surface of the device. The web of fibers is juxtaposed to the image transfer device 18, and high pressure water from manifolds 22 is directed against the outwardly facing surface from jet spaced radially outwardly of the image transfer device 18. The image transfer device 18, and manifolds 22, may be formed and operated in accordance with the teachings of commonly assigned U.S. Pat. No. 4,098,764, No. 5,244,711, No. 5,822,823, and No. 5,827,597, the disclosures of which are hereby incorporated by reference. The entangled fabric can be vacuum dewatered at 24, and dries at an elevated temperature on drying cans 26.

Hydroentanglement results in portions of the precursor web being displaced from on top of the three-dimensional surface elements of the imaging surface to form an imaged and patterned nonwoven fabric. Following the imaging station in FIG. 1, the imaged nonwoven layer can be topically treated with physical performance modifying chemistries as are commonly known and practiced.

EXAMPLES

Example 1

Figure 2:
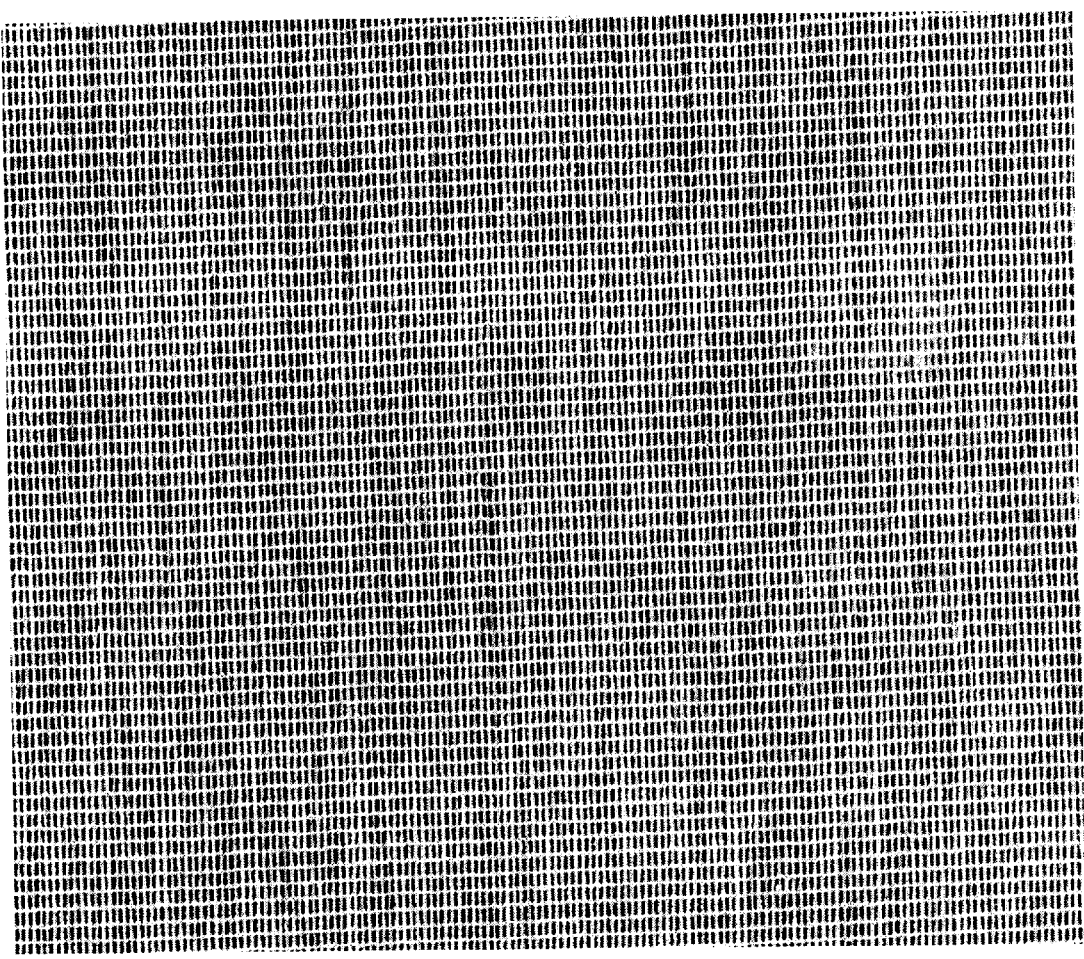
FIG. 2 is photograph of a diaphanous nonwoven fabric made in accordance with the present invention.

A nonwoven fabric was manufactured utilizing the above-described mechanism. The nonwoven fabric comprised a fibrous prebond comprising a 100% by weight cotton fiber. The nonwoven fabric was formed on a flat bed entangler with four entangling manifolds 14 at 300, 300, 800, and 800 pounds per square inch, respectively. The prebond was then run on an image transfer device 18 having an three-dimensional foraminous surface having a 22 by 10 pattern, the result of which is depicted in FIG. 2. Four imaging manifolds were operated at approximately 1600 pounds per square inch each. The material was then dried on elevated temperature steam cans. The final basis weight of the nonwoven fabric was 1.4 ounces per square yard at a rate of 30 yards per minute.

Example 2

A nonwoven fabric as manufactured in Example 1, wherein the prebond comprised a blend of 50% by weight HQ cotton staple fiber and 50% by weight 310P polyester staple fiber. The final basis weight of the nonwoven fabric was 1.4 ounces per square yard at a rate of 30 yards per minute.

Example 3

A nonwoven fabric as manufactured in Example 1, wherein the prebond comprised a layer of HQ cotton staple fiber and a layer of 310P polyester staple fiber. The respective layers each comprise approximately 50% by weight of the overall nonwoven fabric. The cotton layer was positioned in face-to-face juxtaposition with the image transfer device 18 and the polyester layer was positioned opposite to the high pressure imaging manifolds 22. The final basis weight of the nonwoven fabric was 1.4 ounces per square yard at a rate of 30 yards per minute.

Example 4

A nonwoven fabric as manufactured in Example 1, wherein the prebond comprised a layer of HQ cotton staple fiber and a layer of 310P polyester staple fiber. The respective layers each comprise approximately 50% by weight of the overall nonwoven fabric. The polyester layer was positioned in face-to-face juxtaposition with the image transfer device 18 and the cotton layer was positioned opposite to the high pressure imaging manifolds 22. The final basis weight of the nonwoven fabric was 1.4 ounces per square yard at a rate of 30 yards per minute.

The exemplary nonwoven fabrics, and Grade 40 Cheesecloth as available from AAF of Albemarle, N.C., were evaluated in accordance with standard testing methodology. The results of this evaluation are present in Table 1. It has been further identified that the material of the present invention exhibits a more pronounced frictional coefficient when wetted than that of cheesecloth and of the prior art materials. Such retention of the frictional coefficient when wetted is particularly advantageous for applications whereby cleansing or abrading performance is necessary or preferred.

Evaluation of the diaphanous nonwoven fabrics of the present invention in accordance with the teachings of U.S. Pat. No. 5,648,141 find the exemplary materials to have a Calculated Strand Density of less than 0.10 grams per cubic centimeter. The lower bound for Calculated Strand Density for the nonwoven fabric of the present invention is about 0.001 grams per cubic centimeter.

Diaphanous nonwoven fabrics, made in accordance with the present invention, can be used either in rolled sheet form, or as a component fabric in such articles as bandaging, debridement sponges, fenestration pads, and low-linting cleaning articles. Such articles are typified in U.S. Pat. Nos. 6,267,743, 6,290,663, 5,071,648, 5,009,652, 6,199,533, 6,117,515, incorporated herein by reference.

TABLE 1

|  | 40 Grade Cheesecloth | Example 1 | Example 4 |
|---|---|---|---|
| BW (osy) | 1.5 | 1.4 | 1.4 |
| Cotton (% by weight) | 100 | 100 | 50 |
| PET (% by weight) | 0 | 0 | 50 |
| Thickness (mils) | 12.0 | 18.00 | 24.3 |
| Tensile MD (pounds/inch) | 4.1 | 11.4 | 16.6 |
| Tensile CD (pounds/inch) | 11.9 | 5.9 | 12.2 |
| Elongation MD (%) | 26.0 | 20.7 | 47.3 |
| Elongation CD (%) | 66.7 | 112.7 | 133.0 |
| Hand MD (grams) | 18.9 | 84.7 | 16.5 |
| Hand CD (grams) | 4.3 | 11.5 | 2.8 |
| Absorption time (seconds) | 1.0 | 2.8 | 4.7 |
| Absorption capacity (%) | 932 | 1,199 | 1,008 |

What is claimed is:

1. A method of making a diaphanous nonwoven material, comprising the steps of:
    a) providing a synthetic fiber;
    b) providing a natural fiber;
    c) providing a three-dimensional image transfer device;
    d) blending said synthetic fiber and said natural fiber to homogeneity;
    e) forming a fibrous prebond from said blend of fibers;
    f) hydroentangling said precursor web on said image transfer device to form a patterned and imaged nonwoven fabric; and
    g) said nonwoven fabric exhibiting an absorbency of 700% per ounce and a Calculated Strand Density in the range of about 0.001 to about 0.10 grams per cubic centimeter.

2. A method of making a diaphanous nonwoven fabric in accordance with claim 1, wherein the synthetic fiber is selected from the group consisting of thermoplastic fibers, thermoset fibers, and the blends thereof.

3. A method of making a diaphanous nonwoven fabric in accordance with claim 2, wherein the thermoplastic fiber is selected from the group consisting of polyolefins, polyesters, polyamides, and the blends thereof.

4. A method of making a diaphanous nonwoven fabric in accordance with claim 1, wherein the synthetic fiber is selected from natural fibers.

5. A method of making a diaphanous nonwoven fabric in accordance with claim 1, wherein the natural fiber is a cellulosic fiber.

6. A method of making a diaphanous nonwoven fabric in accordance with claim 5, wherein the cellulosic fiber in cotton.

7. A method of making a diaphanous nonwoven fabric in accordance with claim 1, wherein the synthetic fibers are treated with a topical physical performance modifying chemistry.

8. A method of making a diaphanous nonwoven fabric in accordance with claim 1, wherein the synthetic fibers are treated with an internally incorporated physical performance modifying chemistry.

9. A method of making a diaphanous nonwoven fabric in accordance with claim 1, wherein the nonwoven fabric is topically treated with a physical performance modifying chemistry.

10. A method of making a diaphanous nonwoven material, comprising the steps of:
    a) providing a synthetic fiber;
    b) providing a natural fiber;
    c) providing a three-dimensional image transfer device;
    d) layering said synthetic fiber and said natural fiber into a fibrous batt;
    e) forming a fibrous prebond from said fibrous batt;
    f) hydroentangling said precursor web on said image transfer device to form a patterned and imaged nonwoven fabric; and
    g) said nonwoven fabric exhibiting an absorbency of 700% per ounce and a Calculated Strand Density in the range of about 0.001 to about 0.10 grams per cubic centimeter.

* * * * *